US009685906B2

(12) United States Patent
Lagowski et al.

(10) Patent No.: US 9,685,906 B2
(45) Date of Patent: Jun. 20, 2017

(54) PHOTOLUMINESCENCE MAPPING OF PASSIVATION DEFECTS FOR SILICON PHOTOVOLTAICS (71) Applicant: Semilab SDI LLC, Tampa, FL (US)

(72) Inventors: Jacek Lagowski, Tampa, FL (US); Marshall D. Wilson, Tampa, FL (US); Ferenc Korsos, Budapest (HU); György Nádudvari, Pilisszentivan (HU)

(73) Assignee: Semilab SDI LLC, Tampa, FL (US)

( * ) Notice: Subject to any disclaimer, the term of this patent is extended or adjusted under 35 U.S.C. 154(b) by 394 days.

(21) Appl. No.: 14/315,548

(22) Filed: Jun. 26, 2014

(65) Prior Publication Data

US 2015/0008952 A1  Jan. 8, 2015

Related U.S. Application Data (60) Provisional application No. 61/842,857, filed on Jul. 3, 2013.

(51) Int. Cl.
| G01N 21/00 | (2006.01) |
| H02S 50/10 | (2014.01) |
| G01N 21/95 | (2006.01) |
| G01N 21/64 | (2006.01) |
| H02S 50/15 | (2014.01) |

(52) U.S. Cl.
CPC ......... H02S 50/10 (2014.12); G01N 21/6489 (2013.01); G01N 21/9501 (2013.01); H02S 50/15 (2014.12)

(58) Field of Classification Search
CPC .......... G01N 21/00; G06T 7/00; G01M 11/00; H01L 31/00
USPC .................... 356/237.2–237.6, 239.1
See application file for complete search history.

(56) References Cited

U.S. PATENT DOCUMENTS

| 8,064,054 B2 | 11/2011 | Trupke et al. |
| 2002/0030753 A1 | 3/2002 | Kramer et al. |
| 2008/0213926 A1 | 9/2008 | Tajima et al. |
| 2011/0025839 A1 | 2/2011 | Trupke et al. |
| 2011/0234790 A1* | 9/2011 | True ............... H04N 7/183 348/126 |

(Continued)

FOREIGN PATENT DOCUMENTS

| CN | 102736009 | 10/2012 |
| CN | 103808727 | 5/2014 |

(Continued)

OTHER PUBLICATIONS

Chinese Office Action in Chinese Application No. 201410399797.7, dated Oct. 9, 2016, 7 pages.

Primary Examiner — Tarifur Chowdhury
Assistant Examiner — Isiaka Akanbi
(74) Attorney, Agent, or Firm — Fish & Richardson P.C.

(57) ABSTRACT

Methods for fast and accurate mapping of passivation defects in a silicon wafer involve capturing of photoluminescence (PL) images while the wafer is moving, for instance, when the wafer is transported on a belt in a fabrication line. The methods can be applied to in-line diagnostics of silicon wafers in solar cell fabrication. Example embodiments include a procedure for obtaining the whole wafer images of passivation defects from a single image (map) of photoluminescence intensity, and can provide rapid feedback for process control.

15 Claims, 6 Drawing Sheets

(56) References Cited

U.S. PATENT DOCUMENTS

| | | | |
|---|---|---|---|
| 2012/0111396 A1 | 5/2012 | Saylor et al. | |
| 2012/0142125 A1* | 6/2012 | Trupke | G01N 21/6456 |
| | | | 438/16 |
| 2012/0248335 A1 | 10/2012 | Kim et al. | |
| 2013/0016346 A1 | 1/2013 | Romanovsky et al. | |
| 2013/0043405 A1* | 2/2013 | Maxwell | G01N 21/6489 |
| | | | 250/459.1 |
| 2013/0169283 A1* | 7/2013 | Lagowski | G01R 31/305 |
| | | | 324/501 |
| 2014/0234994 A1 | 8/2014 | Abe | |
| 2014/0353523 A1 | 12/2014 | Voronov et al. | |
| 2015/0146193 A1 | 5/2015 | Buczkowski | |
| 2015/0168303 A1* | 6/2015 | Trupke | G01N 21/6456 |
| | | | 324/762.01 |
| 2015/0212011 A1 | 7/2015 | Lombez et al. | |
| 2016/0327485 A1 | 11/2016 | Kiss et al. | |
| 2016/0328840 A1 | 11/2016 | Kiss et al. | |

FOREIGN PATENT DOCUMENTS

| | | |
|---|---|---|
| TW | 201043943 | 12/2010 |
| WO | WO 2012027788 | 3/2012 |
| WO | WO 2014020046 | 2/2014 |

\* cited by examiner

PHOTOLUMINESCENCE MAPPING OF PASSIVATION DEFECTS FOR SILICON PHOTOVOLTAICS

CROSS-REFERENCE TO RELATED APPLICATIONS

Under 35 U.S.C. 119(e), this application claims priority to U.S. Provisional Application No. 61/842,857, entitled "PHOTOLUMINESCENCE MAPPING OF PASSIVATION DEFECTS FOR SILICON PHOTOVOLTAICS," filed on Jul. 3, 2013, the entire contents of which is incorporated herein by reference.

TECHNICAL FIELD

This disclosure relates to testing of silicon wafers, and more particularly to in-line testing of silicon wafers useful for solar cells.

BACKGROUND

During the manufacture of solar cells, poor passivation may result in a presence of localized wafer regions with inferior properties deteriorating cell efficiency. Such typical defects in wafers with passivated emitters are manifested in regions with high emitter saturation current, $J_0$, or low open circuit voltage, $V_{oc}$.

$J_0$ is a parameter that describes losses caused by the recombination of excess carriers (electrons with holes) in the emitter region of a wafer, including surface or interface recombination, and is important for solar cell operation. Passivation is the process designed to reduce such loses. Engineering of effective passivation involves two elements: 1) reduction of the density of interface traps that act as recombination centers; and 2) creation of the electric field barrier that repels one type of carrier from the emitter (for example electrons) preventing the recombination process that requires both type of carriers (electrons and holes).

For very high efficiency thin silicon cells made with high bulk lifetime silicon wafers, the recombination loses of carriers in the bulk silicon (base region) become less important than losses due to recombination in the emitter. For such cells, development of very efficient emitter passivation becomes of increasing importance. The process of passivation is a difficult one. It may be done by deposition of stacked dielectric film structures on the emitter (with top dielectric layer also serving as antireflection coating, ARC). In some high efficiency cells the passivation is done employing amorphous Si layers rather than dielectrics, and the corresponding heterojunction barriers with silicon reduce the recombination. The effectiveness of passivation can be enhanced by hydrogenation and proper post-deposition rapid annealing.

By eliminating the passivation defects, the efficiency of silicon solar cells can be improved, especially for high efficiency cells. This can have a positive impact on competitiveness of silicon photovoltaics in a clean energy market.

An important element in such an effort is the ability to produce whole wafer maps of $J_0$ and $V_{oc}$ (or the implied $V_{oc}$) that are suitable for in-line processing monitoring in silicon PV fabrication.

SUMMARY

Embodiments are disclosed for fast and accurate mapping of passivation defects that can be applied to in-line diagnostics of silicon wafers in solar cell fabrication. The disclosed embodiments are based on capturing of photoluminescence (PL) images while the wafer is moving, for instance, when the wafer is transported on a belt in a fabrication line. Embodiments include a procedure for obtaining the whole wafer images of passivation defects from a single image (map) of photoluminescence intensity, and can provide rapid feedback for process control.

In some embodiments, the whole wafer image is composed from line images consecutively captured on a moving wafer. For each line image, the photoluminescence intensity, PL, emitted from a narrow line across the moving wafer is captured with a line camera. PL capture lines can be perpendicular to wafer movement. Their geometry can be defined by a camera slit or a mechanical slit confining the wafer area seen by the camera. For accurate measurement this narrow line is located within a broader stripe uniformly illuminated with light that excites free carriers and produces photoluminescence. In this manner a steady-state excitation condition is produced on the moving wafer and the steady-state photoluminescence can be captured by monitoring radiation emitted from a narrow line. Short wavelength illumination is used that generates the excess free carriers, electrons, and holes. The photoluminescence is the radiation emitted from the semiconductor as a result of the radiative recombination of photo-generated electrons and holes. The illumination system and photoluminescence capturing systems are stationary and the wafer is moving with respect to them. This enables the capture of consecutive parallel line photoluminescence images on the moving wafer. The whole wafer image is then composed using the consecutive line images captured during the wafer movement. For instance, by capturing 1024 line images with a 1024 pixel line camera a 1024×1024 wafer image is obtained.

In some embodiments, the width of the uniformly illuminated stripe is large enough to produce a constant steady-state excitation line near the stripe center. In these embodiments, the width of the illuminated stripe is substantially larger than the minority carrier diffusion length in measured wafer. This width is also larger than the distance a wafer travels during the excess carrier lifetime and during the time interval used to capture the line image by the camera. On the other hand, a narrow PL capturing line is sufficiently narrow to be located within the constant steady-state excitation region within the excitation stripe. In addition, the capture line is sufficiently narrow to obtain high wafer image resolution in the direction of wafer movement, such as the image consisting of 1024 lines covering the length of wafer. For typical 156 mm×156 mm silicon PV wafer, the width of the excitation stripe can be 10 mm and the capture line width can be 150 μm.

In some embodiments, the image of the emitter saturation current, $J_0$, is obtained from the single image of the inverted photoluminescence intensity, 1/PL, specifically the calibrated G/PL ratio, where G is the generation rate and PL is the photoluminescence intensity count. For quantitative mapping, some embodiments include the calibration of photoluminescence using as a reference the value of $J_0$ independently determined with another measurement technique, for example quasi-steady-state microwave detected photoconductance decay operating within the quality of decay control domain (QSS-μPCD). This is distinctly different from commonly used calibration procedures of the PL signal that are based on an additional multi-parameter measurement of the effective steady-state carrier lifetime $\tau_{eff}$, or the injection level Δn. The described embodiments may carry the advantage of $J_0$ determination from a single PL image captured for one excitation light intensity, for instance at a 2 Sun intensity. This is different than multi-image $J_0$ determination procedures that involve capturing a series of images at different light intensities.

The implied open circuit voltage, implied $V_{oc}$, is obtained also from a single PL intensity image using the logarithm of PL intensity.

Embodiments may provide practical advantages compared to two-dimensional, stationary wafer PL imaging, including 1) lower cost of the line-camera compared to a 2D-camera, and 2) high excitation intensity range achievable with a lower power laser line illumination system as compared to whole wafer 2D illumination system.

Various aspects of the invention are summarized as follows:

In general, in one aspect, the invention features a method of examining a photovoltaic wafer that includes successively illuminating a plurality of illumination regions of a wafer with excitation light while causing relative motion between the wafer and the illumination; detecting photoluminescent light from a plurality of detection regions of the wafer successively illuminated with the excitation light; forming a photoluminescence intensity map of the wafer based on the detected photoluminescent light; and determining information about the wafer based on identifying defects in the wafer based on the photoluminescence intensity map.

Implementations of the method can include one or more of the following features and/or features of other aspects. For example, the information can include identifying defects in the wafer. The method can include fixing the illumination and moving the wafer relative to the illumination. The method can include fixing the wafer and moving the illumination relative to the wafer. The method can include forming an emitter saturation current map of the wafer based on the photoluminescence intensity map. The emitter saturation current map can be formed based on the photoluminescence intensity map, an illumination light generation rate, and a calibration constant. The method can include empirically determining the calibration constant. The method can include forming an open circuit voltage map of the wafer based on the photoluminescence intensity map. The open circuit voltage map can be formed based on the photoluminescence intensity map and an average photoluminescence intensity of the wafer. An illumination region can be the length of the wafer in one dimension and approximately 5 mm in another dimension. An illumination region can be the length of the wafer in one dimension and approximately 8 mm in another dimension. An illumination region can be the length of the wafer in one dimension and approximately 10 mm in another dimension. A detection region can be the length of the wafer in one dimension and approximately 100 μm in another dimension. A detection region can be the length of the wafer in one dimension and approximately 150 μm in another dimension. A detection region can be the length of the wafer in one dimension and approximately 200 μm in another dimension. The photovoltaic wafer can be a passivated silicon photovoltaic wafer. The excitation light can have a wavelength of approximately 804 nm.

In another aspect, the invention features a system for examining a photovoltaic wafer that includes a stage, configured to support the wafer; an energy source; a detector; and a processing module. The detector is fixed relative to the energy source, and the stage and energy source are configured to move relative to one another. When the stage and energy source are moved relative to one another, the energy source is configured to successively illuminate a plurality of illumination regions of a wafer with excitation light. The detector is configured to detect photoluminescent light from a plurality of detection regions of the wafer successively illuminated with the excitation light. The processing module is configured to form a photoluminescence intensity map of the wafer based on the detected photoluminescent light; and determine information about the wafer based on the photoluminescence intensity map.

Implementations of the system can include one or more of the following features and/or features of other aspects. For example, the information can include identifying defects in the wafer. The energy source can be fixed and the stage can be adapted to move relative to the energy source. The excitation light can have a wavelength of approximately 804 nm. The processing module can be configured to form an emitter saturation current map of the wafer based on the photoluminescence intensity map. The processing module can be configured to form the emitter saturation current map based on the photoluminescence intensity map, an illumination light generation rate, and a calibration constant. The processing module can be configured to form an open circuit voltage map of the wafer based on the photoluminescence intensity map. The processing module can be configured to form the open circuit voltage map based on the photoluminescence intensity map and an average photoluminescence intensity of the wafer. The stage can be configured to move the wafer. When the stage and energy source are moved relative to one another, the stage can be configured to move the wafer relative to the energy source.

DETAILED DESCRIPTION

Figure 1A:
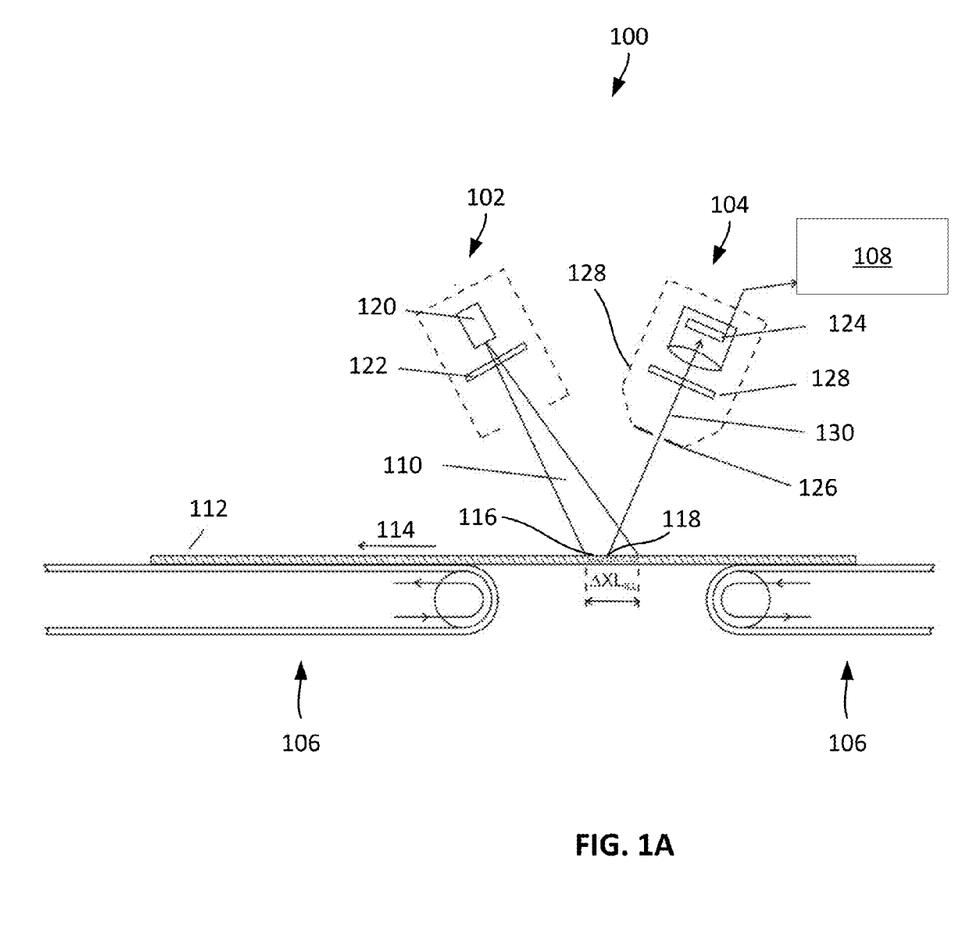
FIG. 1A shows an example embodiment of an imaging system.
Figure 1B:
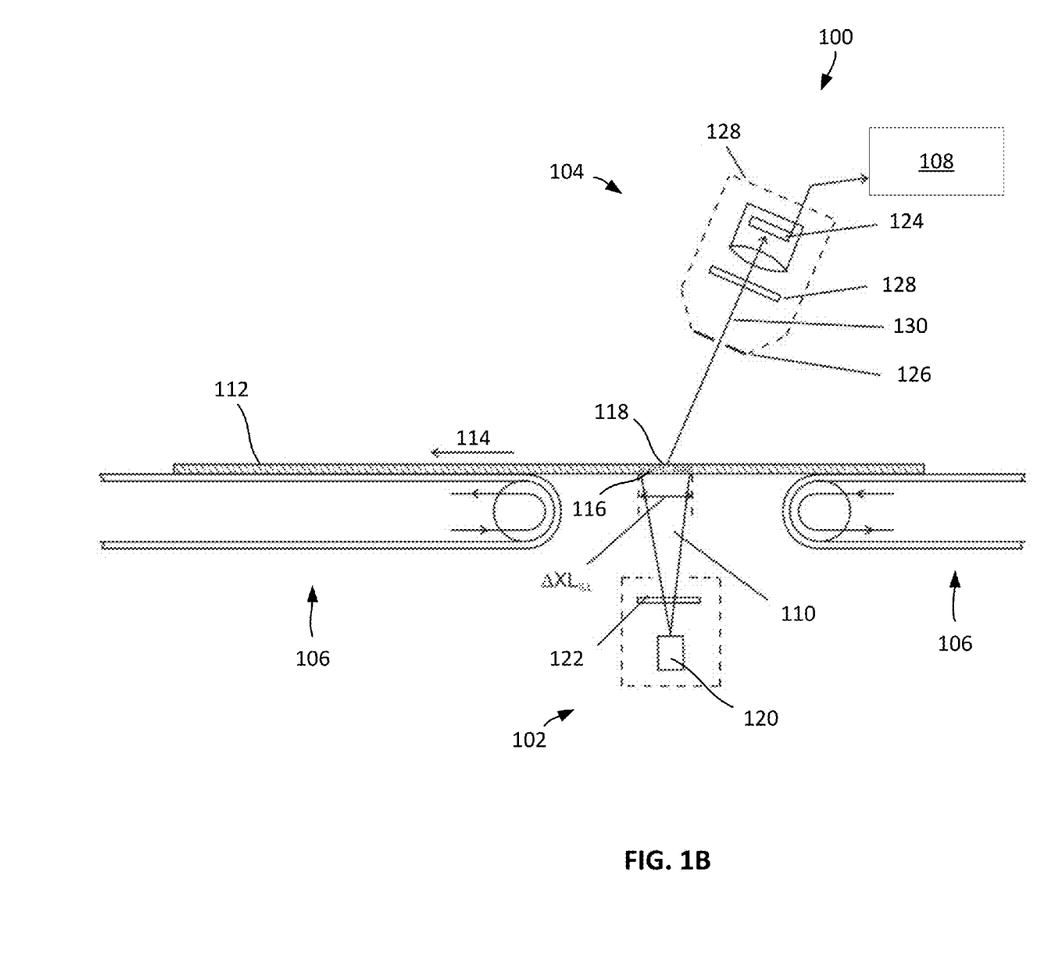
FIG. 1B shows another example embodiment of an imaging system.
Figure 2:
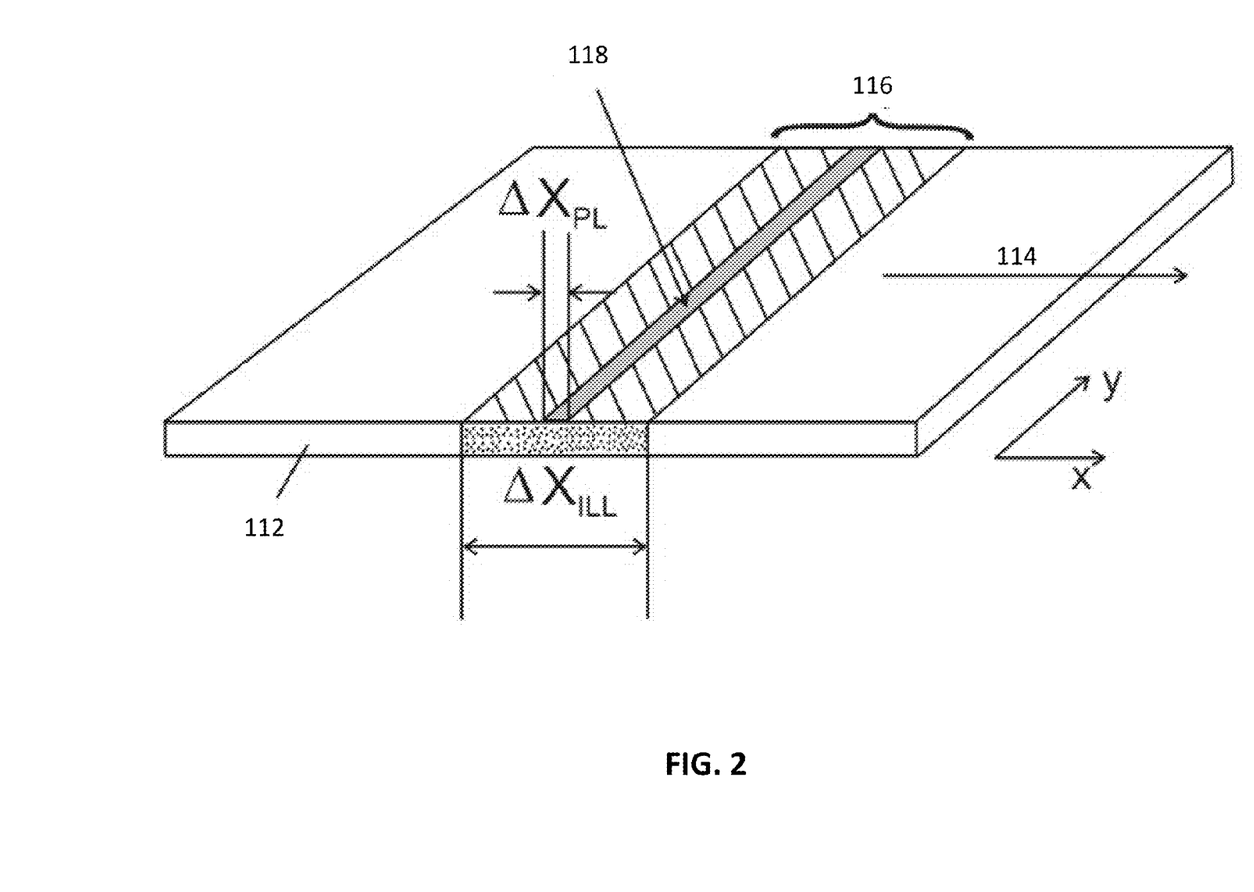
FIG. 2 shows an example of a photoluminescence capture line in relation to an illumination stripe and a wafer.

Referring to FIGS. 1A-B and 2, example embodiments of an imaging system 100 include a line illumination system 102, a photoluminescent (PL) detection system 104, one or more transporting belts 106, and a processing module 108. The line illumination system 102 generates a stationary PL excitation laser beam 110. As a semiconductor wafer 112 is moved along the transporter belts 106 (e.g., in the direction of arrow 114), the laser beam 110 passes over the semiconductor wafer 112, illuminating a portion of the semiconductor wafer 112. Illumination by the laser beam 110 generates photoluminescence in the illuminated portion of the semiconductor wafer 112, producing a photoluminescence excitation stripe 116 with a width $\Delta X_{ILL}$. As the semiconductor wafer 112 continues to move along the transporter belts 106, the laser beam 110 illuminates different portions of the semiconductor wafer 112, causing the photoluminescence excitation stripe 116 to similarly move across the semiconductor wafer 112. During this time, the PL detection system 104 measures photoluminescence along a portion of the stripe 116 (e.g., along a PL capture line 118 with a width $\Delta X_{PL}$ within the stripe 116). Information regarding the measured photoluminescence is transmitted to the processing module 108 for analysis. As an example, the processing module 108 can perform one or more of the calibration and/or analysis techniques described below in order to locate or map passivation defects.

As described above, the line illumination system 102 generates a laser beam 110 that, when used to illuminate the semiconductor wafer 112, generates photoluminescence in the illuminated portion of the semiconductor wafer 112. In an example implementation, the line illumination system 102 generates the laser beam 110 using a PL excitation light source 120 and a filter 122. The PL excitation light source 120 can generate a laser beam having a particular range of frequencies of light. As this laser beam is passed through the filter 122, light having certain wavelengths passes through the filter 122, while light having certain other wavelengths are attenuated or blocked entirely. Thus, the laser beam 110 outputted by the line illumination system 102 includes light having wavelengths substantially within a particular range.

As described above, the PL detection system 104 measures photoluminescence along portions of the semiconductor wafer 112 as the semiconductor wafer 112 moves along the transporting belts 106. In an example implementation, the PL detection system 104 includes a line camera 124 pointed to the stripe 116, such that it can measure photoluminescence along the stripe 116. The PL detection system 104 can also include a PL confining slit 126 (e.g., a slit defined on a housing 128), such that only a limited portion of light can enter the housing 128 and be measured by the line camera 124. For example, the slit 126 can be defined such that only a narrow beam of light 130 originating a limited portion of the stripe 116 (e.g., from the PL capture line 118) can reach the line camera 124. In some implementations, the PL detection system 104 can include also a filter 128, such that only light having a particular wavelength or range of wavelengths can reach the line camera 124. The filter 128 can be selected, in some cases, in order to remove or reduce light from certain wavelengths unrelated to measuring photoluminescence, while preserving light from wavelengths related to measuring photoluminescence. The line camera 124 is communicatively connected to the processing module 108, such that data can be transmitted between the line camera 124 and the processing module 108. In some implementations, information from the line camera 124 (e.g., digital information representing photoluminescence measurements) is transmitted to the processing module 108 for analysis.

The components of system 100 can be arranged in various ways, depending on the implementation. For example, as shown in FIG. 1A, in some implementations, the line illumination system 102 and the PL detection system 104 can both be positioned above the transporting belts 106, such that the laser beam 110 illuminates the semiconductor wafer 112 and the PL detection system 104 measures photoluminescence along the same side of the semiconductor wafer 112. As another example, as shown in FIG. 1B, in some implementations, the line illumination system 102 and the PL detection system 104 can be positioned on opposite sides the transporting belts 106, such that the laser beam 110 illuminates the semiconductor wafer 112 along one side (e.g., the bottom) and the PL detection system 104 measures photoluminescence along another side of the semiconductor wafer 112 (e.g., the top). Other arrangements are possible, depending on the implementation.

As described above, the PL excitation light source 120 and the filter 122 can be selected to generate a laser beam 110 having a particular wavelength or range of wavelengths, such that the laser beam 110 can generate photoluminescence in a particular type of material. For example, the PL excitation light source 120 and the filter 122 can be selected such that the wavelength of the laser beam 110 is short enough to generate excess-free carriers, electrons, and holes in a semiconductor (e.g., for silicon, a typical wavelength used for PL excitation may be about 804 nm). The photogenerated excess-free carriers recombine and also out-diffuse from the illuminated site 122. This creates a lateral decrease of carrier concentration and non-uniform photoluminescence emission. Reliable and accurate measurement of photoluminescence can be performed under the steady-state condition with negligible effect of excess carrier gradients created by lateral free carrier out-diffusion from the generation area (e.g., within the stripe 116). For very short-lifetime as-cut photovoltaic wafers, in some cases, the above condition is easily satisfied for very narrow $\Delta X_{ILL}$=150 µm line laser beams, and the same width of line PL capturing from the entire width of excitation line i.e., having $\Delta X_{PL} \approx \Delta X_{ILL} \approx 150$ µm. For short lifetime wafers, this produces high resolution PL images employed in wafer sorting imaging systems. However, in some cases, these conditions are difficult to satisfy for advanced long lifetime passivated wafers. Long diffusion length L, approaching 1000 µm (i.e., 1 mm) in such wafers, causes inhomogeneous photoluminescence originating from carrier diffusion perpendicular to the line illumination stripe 116. In order to eliminate or reduce this effect, the width of line illumination stripe 116 may be increased to as much as about $\Delta X_{ILL}$=10 mm. In practice, the width of the illumination stripe 116 may be about four times the diffusion length ($\Delta X_{ILL}$=4L) where L is the excess carrier ambipolar diffusion length, typically 1 mm or less. This is in apparent conflict with achieving high resolution PL imaging.

Figure 3:
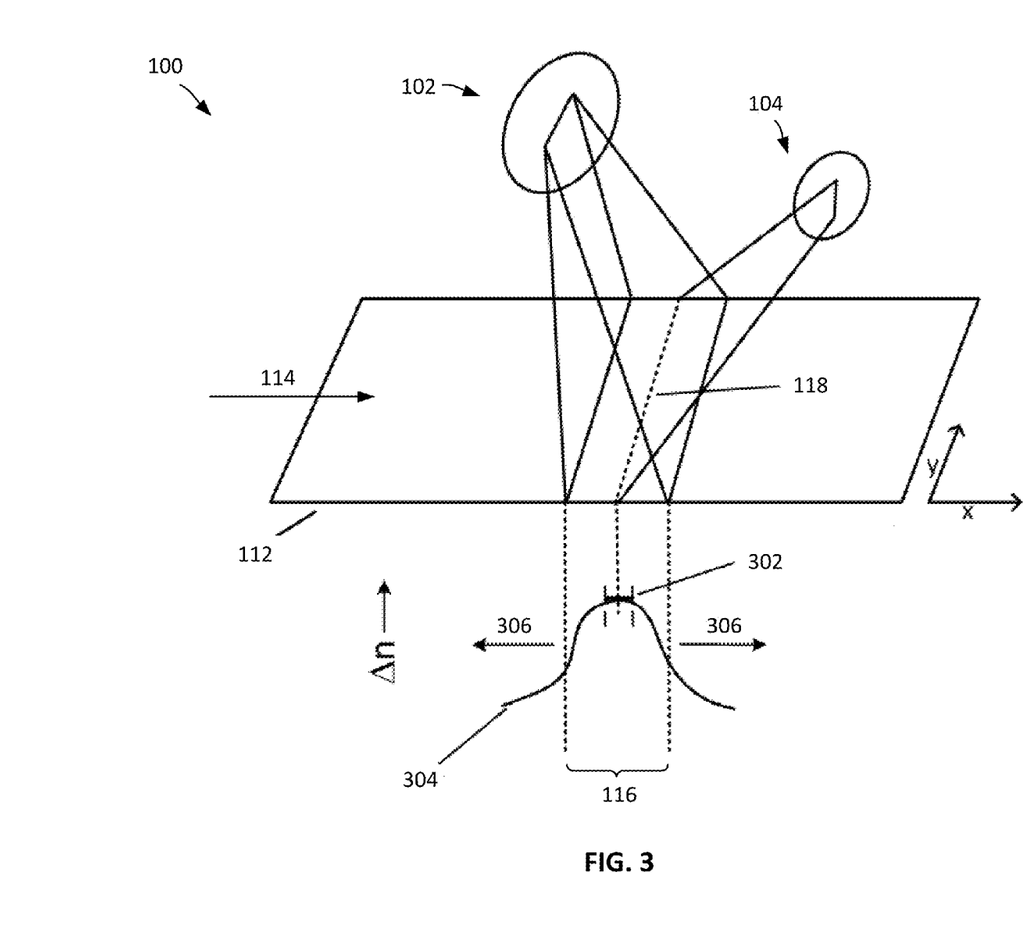
FIG. 3 shows an example illumination and photoluminescence capture geometry and an example profile of photoexcited excess carriers, Δn.

To overcome this conflict, the present disclosure introduces a wide illumination stripe and 116 a narrow PL capturing line 118 with geometry illustrated in FIG. 3. In an example implementation, the line imaging configuration uses a wide illumination stripe 116 (e.g., having $\Delta X_{ILL}$ of 5 cm, 8 cm, or 10 cm) with constant excess carrier concentration within the steady-state zone 302 near the center of the stripe 116. This is illustrated, for example, by the plot 304, which shows the excess carrier, Δn, profile of the semiconductor wafer 112, where arrows 306 indicate lateral diffusion. The width of the steady-state zone 302 is comparable to the value of L. As shown in FIG. 3, the geometry of system 100 limits the PL capture to a narrow line 118 (e.g., having of a width as low as about 150 µm) located within the steady-state zone 302. In an example implementation, for a typical 156×156 mm² silicon PV wafer, a 150 µm line width enables the capture of 1024 PL lines on the wafer moving in the x-direction. Using a line camera with 1024 pixels in the y-direction the desired 1024×1024 image is obtained in this configuration.

Referring to FIGS. 1-3, embodiments of the imaging system 100 can capture the line PL intensity images using a line infrared camera 124, for example a 1024 pixel line InGaAs camera. The filter 128 in front of the camera can be a short pass filter that passes the photoluminescence radiation, but blocks the shorter wavelength excitation light and prevents it from reaching the camera 124.

In some embodiments, the silicon photoluminescence is excited using 804 nm wavelength line laser beam illumination 110. Referring to FIGS. 1-3, embodiments of the imaging system 100 include a filter 122 between the light source 120 and the wafer 112 that can be a short pass filter blocking the long wavelength radiation of the laser spectrum. The illumination light intensity, $I_{ILL}$, can be very uniform within the excitation stripe and it can be adjustable (e.g., in a range between 0.1 Suns, 3 Suns, or 5 Suns or to 10 Suns). Illumination intensity can be calibrated using a NIST certified reference solar cell, as is commonly used in lifetime related measurements for silicon photovoltaics. The generation rate G corresponding to $I_{ILL}$ can be calculated as:

$$G[\text{in cm}^{-3}s^{-1}] = 2.38 \ e17 \frac{I_{ILL}[\text{suns}]}{W[\text{cm}]} R_{opt}$$

where W is the wafer thickness and $R_{opt}$ is the empirical optical factor describing losses due to wafer reflection.

In the constant injection steady-state zone with a concentration of excess carriers, $\Delta n$, the equation describing the photoluminescence intensity $I_{PL}$ is:

$$I_{PL} = C \cdot (N_{dop} + \Delta n) \cdot \Delta n \qquad 1.$$

when C is the calibration constant depending on the radiative recombination efficiency, on the camera set-up and wafer optical factors; $N_{dop}$ is the wafer doping concentration.

In conventional photoluminescence methods, C is determined from independent measurement of $\Delta n$, such as the measurement of the effective steady-state lifetime of excess carriers done for the same generation rate G:

$$\Delta n = \tau_{eff} \cdot G \qquad 2.$$

In some cases, this procedure can be complicated, and it typically involves fitting of many parameters to obtain $\tau_{eff}$.

It also typically requires the averaging of $I_{PL}$ over large area corresponding to the $\tau_{eff}$ measurement.

In some embodiments, a direct calibration is used based on the emitter saturation current, $J_0$. For $I_{ILL}$ range where the emitter recombination is dominant, the steady-state expression for $J_0$ is:

$$J_0 = \frac{Gqn_i^2 W}{(N_{dop} + \Delta n) \cdot \Delta n}. \qquad 3$$

Figure 4:
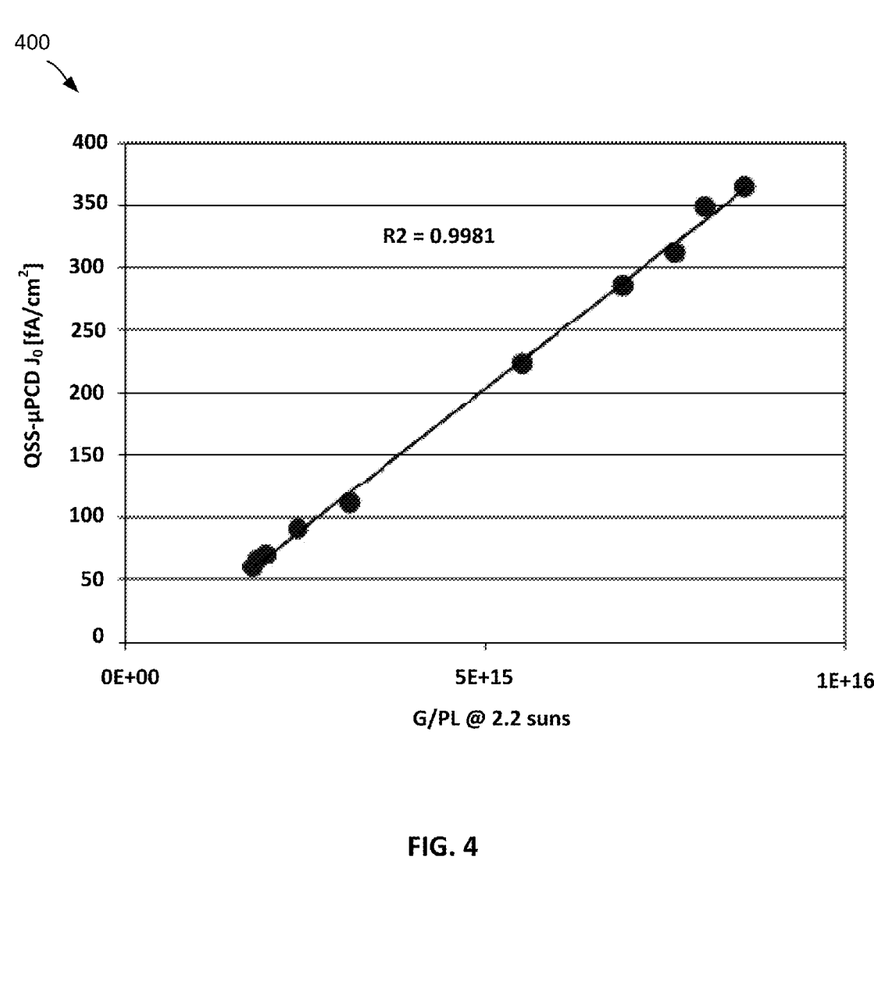
FIG. 4 shows an example relationship between $J_0$ and the G/PL ratio.

The calibration method introduced in this invention uses eqn. 1 and eqn. 3 that are rewritten in the form $$J_0 = A_{cal} \cdot \frac{G}{I_{PL}}. \qquad 4$$

where q is the elementary charge, $n_i$ is the intrinsic carrier concentration and where $A_{cal}$ is the calibration constant. The linear dependence of $J_0$ on $G/I_{PL}$ is illustrated by experimental results shown in plot 400 of FIG. 4. The slope of the line $J_0$ vs. $G/I_{PL}$ gives the calibration constant $A_{cal}$. It is also seen that relationship 4 enables the determination of $J_0$ from a single photoluminescence value $I_{PL}$ at one generation rate G. This corresponds to measurement at one value of the illumination intensity $I_{ILL}$ because G is directly proportional to illumination intensity.

One shall note that the calibration constant determined for one wafer, can be used for other wafers with comparable doping and optical factors (e.g., the reflectivity). It shall also be noted that the wafer thickness cancels in the product $A_{cal} \cdot G$.

In some embodiments, the calibration based on equation 4 can be done using $J_0$ values measured directly with QSS-µPCD and the Basore-Hansen procedure. The $J_0$ values presented in FIG. 4 were obtained with QSS-µPCD on selected wafer sites with different $J_0$ values. The sites were selected from wafer areas uniform over QSS-µPCD probing diameter of about 10 mm. Selecting uniform areas for a calibration reduces the uncertainty caused by differences in resolution between QSS-µPCD and PL imaging.

Determination of $J_0$ directly from the G/PL ratio may provide practical advantages as compared to previous approaches based on PL calibration to QSSPC and multi-image Kane-Swanson $J_0$ extraction, carrying relaxed requirements regarding injection range restriction such as for low injection and high injection. Wafer to wafer recalibration in the present approach would involve optical factor corrections analogous to QSSPC.

The correlations shown in FIG. 4 can be used as an alternative method of passivation defect determination from a single PL image. Based on this correlation, the implied $V_{oc}$ can be obtained from a single image as $$V_{oc} = const + \frac{kT}{q} \ln(PL).$$

Note that the implied $V_{oc}$ is defined as $$V_{oc} = \frac{kT}{q} \ln\left(\frac{\Delta n(N_{dop} + \Delta n)}{n_i^2}\right).$$

The illustrative results shown in FIG. 4 were obtained for silicon PV emitter test structure $p^+/n/p^+$ passivated with $SiO_2/SiN_x$. However, the described embodiments are applicable to abroad range of silicon PV wafers including very high efficiency cell structures passivated with amorphous silicon heterojunction.

Figure 5:
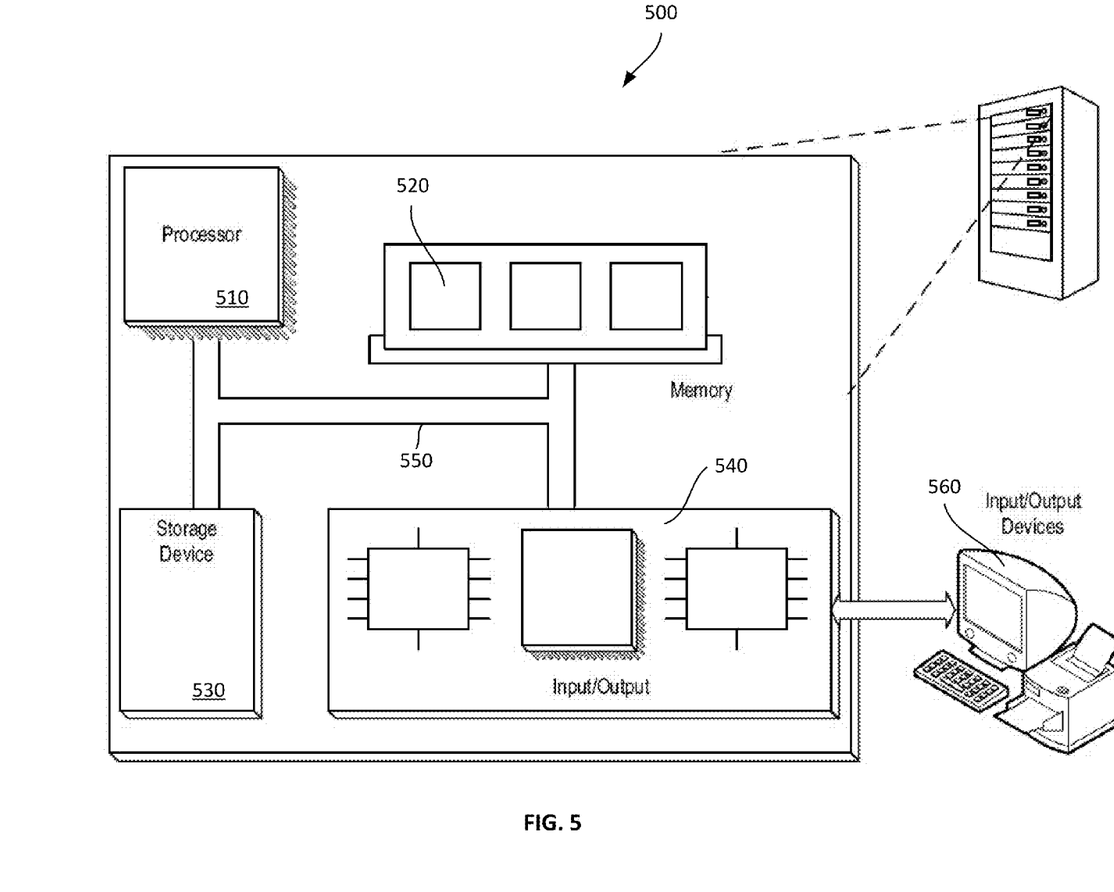
FIG. 5 shows an example computer system.

FIG. 5 is a block diagram of a computer system 500, which is an example of a processing module such as processing module 108 shown above in FIGS. 1 and 2. The system 500 includes a processor 510, a memory 520, a storage device 530, and an input/output device 540. Each of the components 510, 520, 530, and 540 can be interconnected, for example, using a system bus 550. The processor 510 is capable of processing instructions for execution within the system 500. In some implementations, the processor 510 is a single-threaded processor. In some implementations, the processor 510 is a multi-threaded processor. In some implementations, the processor 510 is a quantum computer. The processor 510 is capable of processing instructions stored in the memory 520 or on the storage device 530. The processor 510 may execute operations such as performing one or more of the calibration and/or analysis techniques described above.

The memory 520 stores information within the system 500. In some implementations, the memory 520 is a computer-readable medium. In some implementations, the memory 520 is a volatile memory unit. In some implementations, the memory 520 is a non-volatile memory unit.

The storage device 530 is capable of providing mass storage for the system 500. In some implementations, the storage device 530 is a non-transitory computer-readable medium. In various different implementations, the storage device 530 can include, for example, a hard disk device, an optical disk device, a solid-state drive, a flash drive, magnetic tape, or some other large capacity storage device. In some implementations, the storage device 530 may be a cloud storage device, e.g., a logical storage device including multiple physical storage devices distributed on a network and accessed using a network. In some examples, the storage device may store long-term data. The input/output device 540 provides input/output operations for the system 500. In some implementations, the input/output device 540 can include one or more of a network interface devices, e.g., an Ethernet card, a serial communication device, e.g., an RS-232 port, and/or a wireless interface device, e.g., an 802.11 card, a 3G wireless modem, a 4G wireless modem, etc. A network interface device allows the system 500 to communicate, for example, transmit and receive data. In some implementations, the input/output device can include driver devices configured to receive input data and send output data to other input/output devices, e.g., a keyboard, a mouse, a printer, a sensor (e.g., a sensor that measures component or system-related properties, a sensor that measures environmental-related properties, or other types of sensors), and a display device 560. In some implementations, mobile computing devices, mobile communication devices, and other devices can be used.

A computing system can be realized by instructions that upon execution cause one or more processing devices to carry out the processes and functions described above, for example, storing, maintaining, and displaying artifacts. Such instructions can include, for example, interpreted instructions such as script instructions, or executable code, or other instructions stored in a computer readable medium. A computing system can be distributively implemented over a network, such as a server farm, or a set of widely distributed servers or can be implemented in a single virtual device that includes multiple distributed devices that operate in coordination with one another. For example, one of the devices can control the other devices, or the devices may operate under a set of coordinated rules or protocols, or the devices may be coordinated in another fashion. The coordinated operation of the multiple distributed devices presents the appearance of operating as a single device.

Although an example processing system has been described in FIG. 5, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as performing calibration and/or analysis techniques can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "processing module" may encompass all apparatus, devices, and machines for processing data, including by way of example a programmable processor, a computer, or multiple processors or computers. A processing module can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. Sometimes a server is a general purpose computer, and sometimes it is a custom-tailored special purpose electronic device, and sometimes it is a combination of these things. Implementations can include a back end component, e.g., a data server, or a middleware component, e.g., an application server, or a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

Certain features that are described above in the context of separate implementations can also be implemented in combination in a single implementation. Conversely, features that are described in the context of a single implementation can be implemented in multiple implementations separately or in any sub-combinations.

The order in which operations are performed as described above can be altered. In certain circumstances, multitasking and parallel processing may be advantageous. The separation of system components in the implementations described above should not be understood as requiring such separation.

Other embodiments are in the following claims.

What is claimed is:

1. A method of measuring an emitter saturation current of a photovoltaic wafer using a single image of photoluminescence intensity, the method comprising:
    successively illuminating a plurality of parallel illumination regions of a wafer with excitation light by illuminating an area spanning the wafer in a first direction with excitation light while causing relative motion between the wafer and the illumination in a second direction perpendicular to the first direction, the illuminated area being sufficiently large to generate a steady state photoluminescent condition in at least a portion of the illuminated region;

for each of the illumination regions, detecting photoluminescent light only from a sub-area of the wafer within the illuminated area that exhibits the steady state condition within the wafer in response to the excitation light;

forming a single photoluminescence intensity image of the wafer based on the photoluminescent light detected during a single scan of the wafer relative to the illumination; and determining the emitter saturation current of the wafer based on the single photoluminescence intensity image.

2. The method of claim 1, wherein the relative motion comprises fixing the illumination and moving the wafer relative to the illumination and a detector of the photoluminescent light.

3. The method of claim 1, wherein the relative motion comprises fixing the wafer and moving the illumination and a detector of the photoluminescent light relative to the wafer.

4. The method of claim 1, further comprising forming an emitter saturation current image of the wafer based on inverted photoluminescence intensity values, 1/PL, at different locations of the single photoluminescence intensity image.

5. The method of claim 4, wherein the emitter saturation current image is formed based on a formula $J_0 = A_{cal} \cdot G/PL$, where PL is a photoluminescence intensity at a location on the wafer and G is an illumination light generation rate, and $A_{cal}$ is a calibration constant.

6. The method of claim 5, further comprising empirically determining the calibration constant $A_{cal}$ by comparing values of G/PL at a location on the wafer with a value of the emitter saturation current $J_0$ determined for the same location using another technique.

7. The method of claim 6, wherein the other technique comprises quasi-steady-state microwave detected photoconductance decay operating within a quality of decay control domain (QSS-μPCD).

8. The method of claim 1, further comprising forming an open circuit voltage image of the wafer from a logarithm of the photoluminescence intensity at each wafer location.

9. The method of claim 1, wherein the illuminated area has a dimension of approximately four diffusion lengths or more in the direction of relative motion.

10. The method of claim 9, wherein the illuminated area has a dimension of approximately 10 mm in the direction of relative motion.

11. The method of claim 1, wherein the sub-area of the wafer located approximately at a center of the illuminated area in the direction of relative motion and has a length of approximately 200 μm or less in the direction of the relative motion and extends the length of the wafer in the first direction.

12. The method of claim 11, wherein length of the wafer in one dimension and of the sub-area is approximately 100 μm in the direction of the relative motion another dimension.

13. The method of claim 1, wherein the photovoltaic wafer is a passivated silicon photovoltaic wafer.

14. The method of claim 13, wherein the photovoltaic silicon wafer comprises a passivated emitter surface layer.

15. The method of claim 1, wherein the excitation light has a wavelength of approximately 804 nm and an intensity in a range between 0.1 Suns and 10 Suns.

* * * * *

UNITED STATES PATENT AND TRADEMARK OFFICE
CERTIFICATE OF CORRECTION

PATENT NO.       : 9,685,906 B2
APPLICATION NO.  : 14/315548
DATED            : June 20, 2017
INVENTOR(S)      : Jacek Lagowski et al.

Page 1 of 1

It is certified that error appears in the above-identified patent and that said Letters Patent is hereby corrected as shown below:

Column 12, Line 24, Claim 12, delete "of the wafer in one dimension and";

Column 12, Line 25, Claim 12, delete "motion another dimension." and insert --motion.--.

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*